(12) United States Patent
Liang et al.

(10) Patent No.: US 10,536,617 B2
(45) Date of Patent: Jan. 14, 2020

(54) DUAL-VIEW PROBE FOR ILLUMINATION AND IMAGING, AND USE THEREOF

(71) Applicant: The Arizona Board of Regents on behalf of the University of Arizona, Tucson, AZ (US)

(72) Inventors: Rongguang Liang, Tucson, AZ (US); Bhaskar Banerjee, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 592 days.

(21) Appl. No.: 14/960,029

(22) Filed: Dec. 4, 2015

(65) Prior Publication Data

US 2016/0088204 A1 Mar. 24, 2016

Related U.S. Application Data

(63) Continuation-in-part of application No. PCT/US2014/039619, filed on May 27, 2014.
(Continued)

(51) Int. Cl.
*H04N 5/225* (2006.01)
*G02B 23/24* (2006.01)
(Continued)

(52) U.S. Cl.
CPC ........... *H04N 5/2256* (2013.01); *A61B 1/012* (2013.01); *A61B 1/04* (2013.01); *A61B 1/0615* (2013.01);
(Continued)

(58) Field of Classification Search
CPC .... H04N 5/2256; G02B 23/26; A61B 1/0607; A61B 1/0615
See application file for complete search history.

(56) References Cited

U.S. PATENT DOCUMENTS 3,404,934 A 10/1968 Brachvogel et al.
4,146,019 A 3/1979 Bass et al.
(Continued)

FOREIGN PATENT DOCUMENTS

CN 102209926 A 10/2011
EP 2716207 A1 4/2014
(Continued)

OTHER PUBLICATIONS

Chinese Office Action dated Mar. 22, 2017, issued in Chinese Application No. 201480037378.7, filed May 27, 2014, 14 pages.
(Continued)

*Primary Examiner* — Mainul Hasan
(74) *Attorney, Agent, or Firm* — Barry L. Davison; Davis Wright Tremaine LLP

(57) ABSTRACT

One embodiment of the invention is directed to an imaging probe which comprises a first element supplying electromagnetic radiation in a forward path for illuminating a forward field of view of space in front of the probe, a second element supplying electromagnetic radiation in a sideways and/or rearward path for illuminating a sideways and/or back field of view of space alongside the probe and an image sensor. The probe further includes an imaging device in imaging paths imaging the forward and sideways and/or back fields of view onto the image sensor. Preferably the forward path, the sideways and/or rearward path and the imaging paths are unobstructed by any component of the probe. Preferably the forward and sideways and/or back fields of view are registered in a fixed spatial relationship relative to one another on the image sensor. This probe can also be used with existing endoscopes or laparoscopes so that it will be easily merged into current instruments of different manufacturers, making it easier and cheaper to use this product without the expense of a totally new endoscopy
(Continued)

or laparoscope platform. This probe can also be used to image objects in inanimate environments as well, such as in containers, buildings, rooms, engines and pipes.

38 Claims, 9 Drawing Sheets

Related U.S. Application Data

(60) Provisional application No. 61/831,438, filed on Jun. 5, 2013.

(51) Int. Cl.
*A61B 1/317* (2006.01)
*A61B 1/06* (2006.01)
*A61B 1/04* (2006.01)
*A61B 1/313* (2006.01)
*G02B 23/26* (2006.01)
*A61B 1/012* (2006.01)

(52) U.S. Cl.
CPC .......... *A61B 1/0623* (2013.01); *A61B 1/317* (2013.01); *A61B 1/3132* (2013.01); *G02B 23/2461* (2013.01); *G02B 23/2484* (2013.01); *G02B 23/26* (2013.01); *H04N 2005/2255* (2013.01)

(56) References Cited

U.S. PATENT DOCUMENTS

| | | | |
|---|---|---|---|
| 5,822,057 A * | 10/1998 | Samman | G02B 23/26 356/241.1 |
| 9,486,123 B2 | 11/2016 | Morita | |
| 9,554,097 B2 | 1/2017 | Sasaki | |
| 2004/0254424 A1 | 12/2004 | Simkulet | |
| 2004/0264013 A1 | 12/2004 | Matsuki et al. | |
| 2006/0069314 A1 | 3/2006 | Farr | |
| 2006/0217593 A1 | 9/2006 | Gilad et al. | |
| 2008/0045797 A1 | 2/2008 | Yasushi | |
| 2008/0208006 A1 * | 8/2008 | Farr | A61B 1/0607 600/178 |
| 2008/0247039 A1 | 10/2008 | Mizusawa | |
| 2009/0082629 A1 * | 3/2009 | Dotan | A61B 1/00096 600/160 |
| 2010/0198009 A1 * | 8/2010 | Farr | A61B 1/00103 600/109 |
| 2010/0312057 A1 | 12/2010 | Konno | |
| 2013/0137923 A1 * | 5/2013 | Honda | G02B 23/2469 600/109 |

FOREIGN PATENT DOCUMENTS

| | | |
|---|---|---|
| JP | 2007-307090 A | 11/2007 |
| JP | 2008-257123 A | 10/2008 |
| JP | 2011-152202 A | 8/2011 |
| JP | 2012-090723 A | 5/2012 |
| WO | 2007/126429 A2 | 11/2007 |
| WO | 2012/165203 A1 | 12/2012 |
| WO | 2012/165204 A1 | 12/2012 |
| WO | 2013033811 A1 | 3/2013 |
| WO | 2013/047215 A1 | 4/2013 |

OTHER PUBLICATIONS

Arber et al., "Proof-of-concept study of the Aer-O-Scope omnidirectional colonoscopic viewing system in ex vivo and in vivo porcine models," Endoscopy, 39(5), 2007, pp. 412-417.

Demarco et al., "Impact of experience with a retrograde-viewing device on adenoma detection rates and withdrawal times during colonoscopy: the Third Eye Retroscope study group," Gastrointestinal Endoscopy, 71(3), Mar. 2010, pp. 542-550.

International Search Report and Written Opinion issued in International Patent Application No. PCT/US2014/039619, dated Oct. 16, 2014, 16 pages.

Ma et al., "C-view omnidirectional endoscope for minimally invasive surgery/disgnostics," Proc. SPIE, Medical Imaging 2007: Visualization and Image-Guided Procedures, 65090C, Mar. 22, 2007.

Peery et al., "Burden of gastrointestinal disease in the United States: 2012 Update," Gastroenterology, 143(5), Nov. 2012, pp. 1179-1187.e3.

Rex, "Third Eye Retroscope: rationale, efficacy, challenges," Reviews in Gastroenterological Disorders, 9(1), 2009, pp. 1-6.

Sagawa et al., "Omnidirectional Vision Attachment for Medical Endoscopes," The 8th Workshop on Omnidirectional Vision, Camera Networks and Non-classical Cameras—OMNIVIS, Oct. 2008, Marseille, France, 14 pages.

Wang et al., "Development of a catadioptric endoscope objective with forward and side views," Journal of Biomedical Optics, 16(6), Jun. 2011, pp. 066015-1-066015-15.

Waye et al., "A retrograde-viewing device improves detection of adenomas in the colon: a prospective efficacy evaluation (with videos)," Gastrointestinal Endoscopy, 71(3), Mar. 2010, pp. 551-556.

European Extended Search Report dated Dec. 20, 2016, issued in European Patent Application No. 14806952.9, filed May 27, 2014, 10 pages.

\* cited by examiner

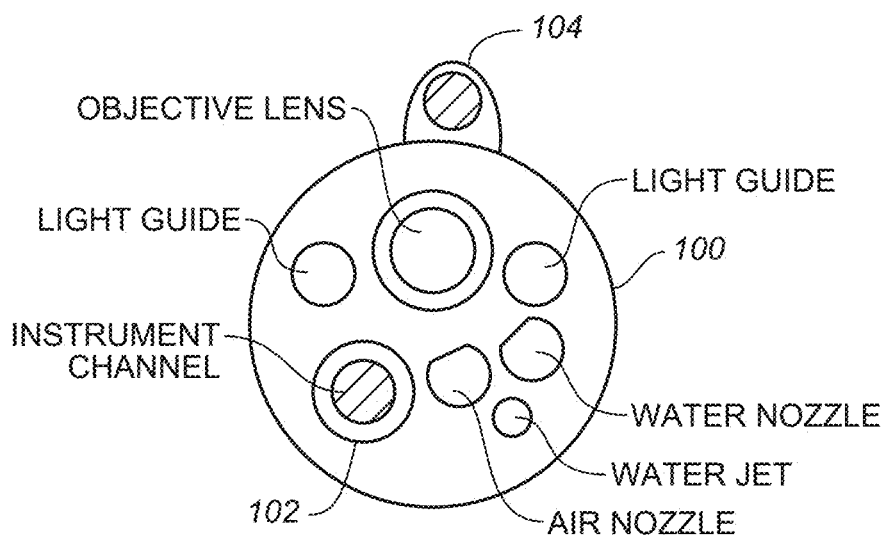
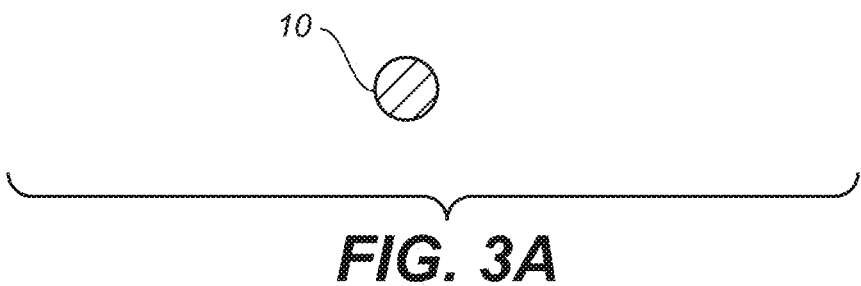
FIG. 3A
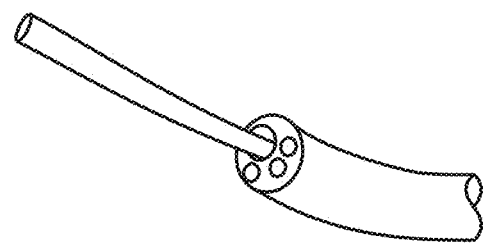
FIG. 3B

DUAL-VIEW PROBE FOR ILLUMINATION AND IMAGING, AND USE THEREOF

CROSS-REFERENCE TO RELATED APPLICATIONS

This application is a continuation-in-part of International Application No. PCT/US2014/039619 filed May 27, 2014, which claims priority to U.S. Provisional Application No. 61/831,438, filed Jun. 5, 2013.

FIELD OF THE INVENTION

The current invention is a design for a novel dual-view probe which includes front, sideways and rear view illumination and imaging, and method for using the probe. In some of the embodiments, the probe provides omnidirectional sideways and rear view and multimodal capability and can help detect lesions or other structures in living organisms that are hidden from the front view or are difficult to see. In other embodiments, the probe can be used to simultaneously illuminate and image inanimate, inorganic objects such as a container, building, room, engine, piping directly or through a limited opening.

BACKGROUND OF THE INVENTION

Colorectal cancer is the second leading cause of cancer death in the United States and colonoscopy is the preferred screening procedure, with about 12 million procedures performed per year. Please see Peery A F, Dellon E S, Lund J, et al. Burden of gastrointestinal disease in the United States: 2012 update. *Gastroenterology*. November 2012; 143 (5): 1179-1187. However, standard colonoscopy is far from perfect as standard forward-viewing endoscopes are unable to visualize polyps hidden by haustral folds and flexures of the colon as illustrated in FIG. 1, where (a) the forward view shows no polyps, but when the tip of the scope is sharply bent to look backwards, which is not often possible, (b) a polyp hidden behind a fold is easily seen. Well over 20% of polyps can be missed during colonoscopy and some of these lead to unexpected cancers.

Lesions are missed because they are i) hidden from forward view and ii) because they have poor color contrast. New methods of improving visualization, such as wide-angle colonoscopy, cap-assisted colonoscopy, the Aer-O-Scope, and Third Eye Retroscope (TER) have not consistently improved polyp detection and have not been clinically accepted. Please see, for example, Arber N, Grinshpon R, Pfeffer J, Maor L, Bar-Meir S, Rex D. Proof-of-concept study of the Aer-O-Scope™ omnidirectional colonoscopic viewing system in ex vivo and in vivo porcine models. Endoscopy. May 2007; 39(5):412-417; Rex D K. Third Eye Retroscope: Rationale, Efficacy, Challenges. Rev Gastroenterol Disord. Winter 2009; 9(1):1-6; Waye J D, Heigh R I, Fleischer D E, et al. A retrograde-viewing device improves detection of adenomas in the colon: a prospective efficacy evaluation (with videos). Gastrointestinal Endoscopy. March 2010; 71(3):551-556. There is an unmet need for an easy to use endoscope or endoscopic probe that can be easily incorporated into current endoscopes to improve lesion detection, prevent more cancers, and lengthen screening intervals. There is also a need for providing backward and/or sideway vision during medical procedures including laparoscopic surgery, robotic surgery arthroscopy and images of body cavities such as the paranasal sinuses.

Prior art designs for solving the above problems suffer from obstructions either by the detector optics partially obstructing the illumination or by the illumination optics partially obstructing the detector. Please see Waye J D, Heigh R I, Fleischer D E, et al. A retrograde-viewing device improves detection of adenomas in the colon: a prospective efficacy evaluation (with videos). Gastrointestinal Endoscopy. March 2010; 71(3):551-556; Wang R C C, Deen M J, Armstrong D, Fang Q Y. Development of a catadioptric endoscope objective with forward and side views. Journal of Biomedical Optics. June 2011; 16(6); Ma J, Simkulet M, Smith J. C-view omnidirectional endoscope for minimally invasive surgery/diagnostics. SPIE Proceedings. 2007; 6509:65090C; Ryusuke S, Takarou E, Tomio Y. Omnidirectional vision attachment for medical endoscopes. OMNIVIS08. 2008:1-14.

Dual-view objective lenses (also called "objectives") have been studied by a few research groups. However, the reported dual-view objectives do not have built-in illumination systems. Please see Waye J D, Heigh R I, Fleischer D E, et al. A retrograde-viewing device improves detection of adenomas in the colon: a prospective efficacy evaluation (with videos). Gastrointestinal Endoscopy. March 2010; 71(3):551-556; Wang R C C, Deen M J, Armstrong D, Fang Q Y. Development of a catadioptric endoscope objective with forward and side views. Journal of Biomedical Optics. June 2011; 16(6); Ma J, Simkulet M, Smith J. C-view omnidirectional endoscope for minimally invasive surgery/diagnostics. SPIE Proceedings. 2007; 6509:65090C; Ryusuke S, Takarou E, Tomio Y. Omnidirectional vision attachment for medical endoscopes. OMNIVIS08. 2008:1-14. Instead, they rely solely on the external illumination of the standard colonoscope. Consequently, the retrograde view is partially blocked by the colonoscope itself and the forward view of the colonoscope is partially blocked by the rear view retroscope.

Some endoscope designs use two different monitors, one for the forward view and one for the rear view, requiring the physician to watch two screens at the same time, and making it difficult for the physician to register and localize images. Please see DeMarco D C, Odstrcil E, Lara L F, et al. Impact of experience with a retrograde-viewing device on adenoma detection rates and withdrawal times during colonoscopy: the Third Eye Retroscope study group. Gastrointestinal endoscopy. March 2010; 71(3):542-550.

Dual-view imaging probes are also useful for detecting lesions or other structures not visible with forward-viewing-only instruments in other parts of the human body such as sinuses, the duodenenum, the alimentary tract, the thorax, in robotic surgery, and in natural orifice transluminal endoscopic surgery (NOTES). When a forward viewing instrument is used to inspect a portion of an alimentary tract in a tight curve, for example, the curvature of the portion may cause the instrument to slip rapidly in the tract, preventing the inner curved surface of the portion to be inspected when only the forward view is available.

Endoscopes are used for non-biological applications to visually inspect structures through a small opening, in which case these devices are known as borescopes. Structures and spaces are commonly inspected using fiber or video scopes, through a small or limited opening without dismantling an apparatus or machinery. Visual inspection is often the first mode of non-destructive testing, it is commonly used in a range of industries, including: aerospace, automobile, manufacturing, power-generation, oil and gas, transportation, electronics and computer hardware.

Borescopes are used to inspect aircraft and automobile engines quickly without the time consuming process of taking apart the complex machinery. Similarly, areas of piping and compartments in power stations that cannot be easily entered can be visually inspected using borescopes. Manufacturing processes frequently need remote visual inspection, as well as for the maintenance of complex machinery and the monitoring of processes in a clean environment.

Borescopes are generally forward viewing, or have limited ability to deflect the tip to look sideways or partly backwards. The tips of flexible borescopes can be deflected to allow inspections to the sides or at a different angle from the forward view. Some borescopes have interchangeable heads that enable alternate views, such as to the sides or at an angle backwards. The need to use interchangeable tips leads to lengthening of the inspection process and the components require repairs or need to be replaced. Current borescopes, with or without interchangeable heads, do not have the capability to simultaneously illuminate and provide a combined forward and backward/side view.

It is therefore desirable to provide a dual-view imaging probe that can overcome the above difficulties.

SUMMARY OF THE INVENTION

The invention described herein addresses the concerns described above, by simultaneously imaging parts of the body such as the colon in forward view as well as backward view, preferably with 360 degree omnidirectional back field of view. Preferably these views are supplemented with high contrast imaging techniques to maximize polyp detection or detection of other lesions or structures for a transformational impact on colorectal cancer and other types of diseases.

One embodiment of the invention is directed to an imaging probe which comprises a cylindrical light guide supplying electromagnetic radiation in a forward path for illuminating a forward field of view of space in front of the probe, an array of optical fibers surrounding the cylindrical light guide and a ring reflector reflecting electromagnetic radiation from the array in sideways and/or rearward paths for illuminating a back field of view of space alongside the probe. The probe further includes an image sensor and an objective in imaging paths imaging the front, sideways and/or back fields of view onto the image sensor so that the forward, sideways and/or back fields of view are registered in a fixed spatial relationship relative to one another on the image sensor, wherein the forward path, the sideways and/or rearward paths and the imaging paths are unobstructed by any component of the probe. In this document, the terms "rear", "rearward", "back", and "backward" may be used interchangeably, as may "front", "in front of," and "forward."

Another embodiment of the invention is directed to an imaging probe which comprises a first element supplying electromagnetic radiation in a forward path for illuminating a forward field of view of space in front of the probe, a second element supplying electromagnetic radiation in a sideways and/or rearward path for illuminating a back field of view of space alongside the probe and an image sensor. The probe further includes an imaging device in imaging paths imaging the forward, sideways and/or back fields of view onto the image sensor, wherein the forward path, the sideways and/or rearward path and the imaging paths are unobstructed by any component of the probe.

Yet another embodiment of the invention is directed to an imaging probe comprising a first element supplying electromagnetic radiation in a forward path for illuminating a forward view of space in front of the probe and a second element supplying electromagnetic radiation in a sideways and/or rearward path for illuminating a back field of view of space alongside the probe. The probe further includes an image sensor and an imaging device in imaging paths imaging the forward and sideways and/or back fields of view onto the image sensor so that the forward and sideways and/or back fields of view are registered in a fixed spatial relationship relative to one another on the image sensor.

An additional embodiment of the invention is directed to a medical instrument comprising a housing defining a plurality of channels therein and an imaging probe in one of said channels or attached to the housing. The imaging probe comprises a first element supplying electromagnetic radiation in a forward path for illuminating a forward view of space in front of the probe and a second element supplying electromagnetic radiation for illuminating a sideways and/or back field of view of space alongside the probe and in a sideways and/or rearward path. The imaging probe further includes an image sensor and an imaging system in imaging paths imaging the forward and sideways and/or back fields of view onto the image sensor, wherein the forward path, the sideways and/or rearward path and the imaging paths are unobstructed by any component of the probe.

Yet another embodiment of the invention is directed to an imaging method which comprises supplying electromagnetic radiation in a forward path for illuminating a forward field of view of space in front of the probe, supplying electromagnetic radiation in a sideways and/or rearward path for illuminating a sideways and/or back field of view of space alongside the probe and imaging along imaging paths the forward and sideways and/or back fields of view onto an image sensor, wherein the forward path, the sideways and/or rearward path and the imaging paths are unobstructed.

One more embodiment is directed to an imaging method comprising imaging along a forward path a forward field of view of space in front of the probe onto an image sensor; and imaging along a sideways and/or rearward path a sideways and/or back field of view of space alongside the probe onto the image sensor so that the forward and sideways and/or back fields of view are registered in a fixed spatial relationship relative to one another on the image sensor.

All patents, patent applications, articles, books, specifications, standards, other publications, documents and things referenced herein are hereby incorporated herein by this reference in their entirety for all purposes. To the extent of any inconsistency or conflict in the definition or use of a term between any of the incorporated publications, documents or things and the text of the present document, the definition or use of the term in the present document shall prevail.

BRIEF DESCRIPTION OF THE DRAWINGS

FIG. 3A is a cross-sectional view of an endoscope with channels for housing an imaging probe to illustrate another embodiment of the invention.

FIG. 3B is a perspective view of the distal end of the endoscope of FIG. 3A.

Identical components in this application are labeled by the same numerals.

DETAILED DESCRIPTION OF EXEMPLARY EMBODIMENTS

Figure 1:
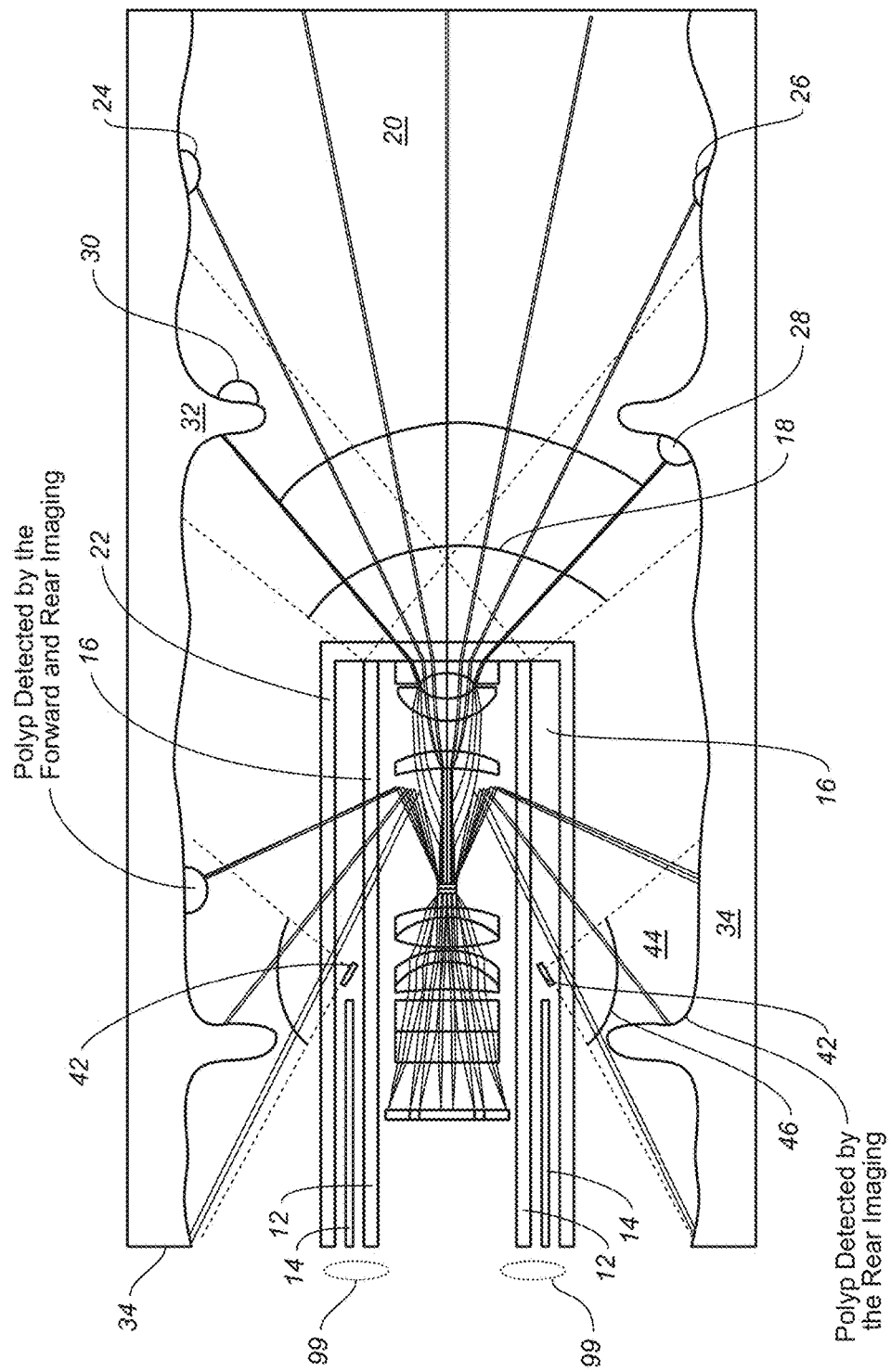
FIG. 1 is a cross-sectional view of an imaging probe to illustrate one embodiment of the invention, where forward, sideways and rearward illumination paths are illustrated.

Some of the embodiments of the invention described herein address and meet the deficiencies with prior designs in a novel way that would be welcomed by physicians, third party payers, and endoscope and endoscope accessory instrument manufacturers world-wide for a major impact in one of the most common cancers.

In one of the embodiments, the electromagnetic radiation from the fiber array is re-directed to the sideways and rear fields of view by a ring reflector so that it can omnidirectionally illuminate the regions hidden from forward-viewing endoscopes by the haustral folds and flexures of the colon. The electromagnetic radiation for forward illumination is guided from another fiber array to the endoscope tip by the hollow cylindrical light guide using the principle of total internal reflection (TIR). The hollow cylindrical light guide can be made of optical plastic or glass. A catadioptric objective is designed so that the forward imaging is imaged upon the central field of the sensor and the 360 degree omnidirectional sideways and rear imaging is imaged upon the outer field of the sensor. This design provides unobstructed illumination and imaging of the colon in forward, sideways and backward directions and generates high contrast multimodal images in a single display. Probe 10 can also be used for imaging parts of the body other than the colon, such as cavities in the body where obtaining simultaneous forward and rearward views are important for diagnosis.

Multimodal polarized light (such as white light) and autofluorescence imaging modalities utilize unique and complementary contrast mechanisms to improve the detection of polyps, including sessile and flat lesions that are difficult to see. Autofluorescence uses structural and metabolic changes in neoplasms to generate images with high contrast. Polarized light imaging removes specular reflection from the tissue surface, water, and mucin and increases image contrast. The addition of polarized electromagnetic radiation and autofluorescence imaging further enhances lesion detection in such a dual-view endoscope or probe.

This innovative probe can be used with existing endoscopes, being easily merged into current instruments of different manufacturers, making it easier and cheaper for endoscopists to use this product without the expense of a totally new endoscopy platform. The novel design can be adapted to develop endoscopes for imaging other organs including sinuses, lungs, and joint cavities, as well as during laparoscopic and robotic surgery, as well as NOTES, to allow the surgeon to view structures not normally seen with forward viewing instruments. The probe can be passed through the biopsy channel of a standard endoscope or the technology can be built into a dedicated endoscope.

The multimodal dual-view endoscopic probe in some embodiments of this invention has unique illumination and objective lens designs that provides simultaneous forward, sideways and rear illumination and multimodal imaging without obscuring the field of view. Prior art designs suffer from obstructions either by the detector optics partially obstructing the illumination or by the illumination optics partially obstructing the detector, as noted above.

FIG. 1 is a cross-sectional view of an imaging probe 10 to illustrate one embodiment of the invention, where forward sideways and rearward illumination paths are illustrated. Two rings or arrays 12 and 14 of optical fibers are used to supply electromagnetic radiation to the forward and rearward illumination paths respectively. The electromagnetic radiation from ring 12 is guided (towards the right hand side in FIG. 1) by the hollow light guide 16 to the front end of the probe 10, and emerges as rays 18 to illuminate space 20 in front of the probe. In this manner, the forward field of view of the probe 10 is illuminated. Ring 12, hollow light guide 16 and front and rear lens groups are contained within and supported by an optical dome 22. The electromagnetic radiation for forward field of view illumination is guided from ring 12 to emerge as rays 18 at the front end of the probe 10 by the hollow cylindrical light guide 16 using the principle of total internal reflection (TIR). The hollow cylindrical light guide can be made of optical plastic or glass. The angular span of illumination rays 18 can be tailored for specific applications.

Both the light guide and optical dome are optically transparent and do not block the illumination and imaging fields. The illumination and imaging paths are separated to minimize stray light from the optical elements inside the dome. A single video image is provided for the physician, providing a unique aspect of this embodiment. As shown in FIG. 1, the forward illumination path 18 illuminates polyps 24, 26 and 28, but is unable to shed light on polyp 30 hidden behind a fold 32 in the colon 34. To illuminate polyps hidden behind folds, the electromagnetic radiation from the fiber ring or array 14 is re-directed to the sideways and rear or back field of view by a ring reflector 42 along paths 46 so that it omnidirectionally illuminates space 44 alongside the probe and the regions hidden from forward viewing endoscopes by the folds such as fold 32. As shown in FIG. 1, the electromagnetic radiation from ring reflector 42 illuminates regions to the side of as well as to the back of probe 10. Depending on the angle of ring reflector 42 relative to the colon wall, the regions illuminated can reside only to the side of probe 10 or mostly to the rear of probe 10. The ring reflector 42 may be mounted on the cylinder tube 16 in a manner known to those skilled in the art. Just as with the forward illumination, the rearward illumination angle can be tailored for specific applications.

Figure 2:
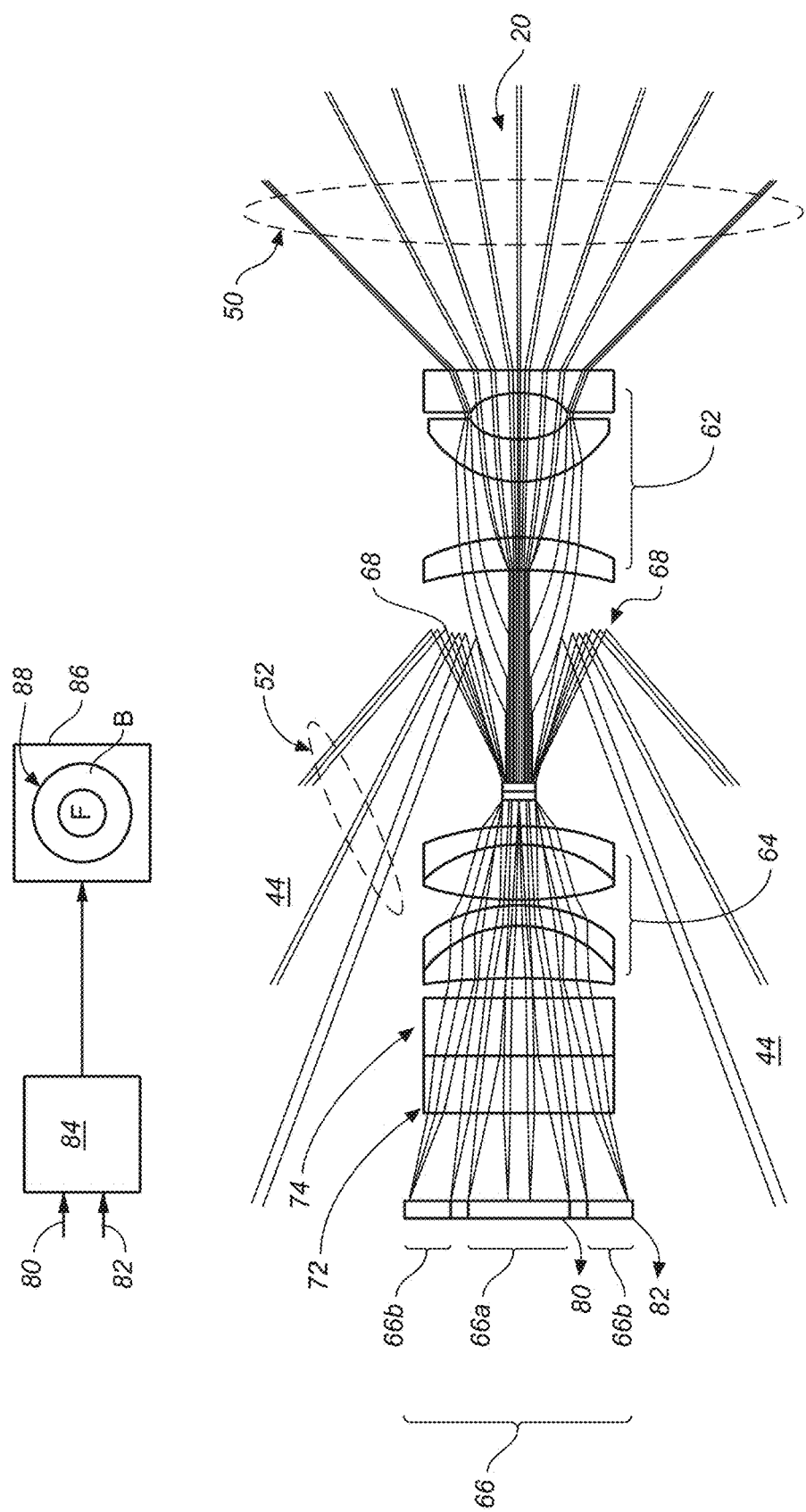
FIG. 2 is a cross-sectional view of some components of the imaging probe of FIG. 1, where forward, sideways and rearward imaging paths are illustrated.

FIG. 2 is a cross-sectional view of some components of the imaging probe of FIG. 1, where forward imaging path 50 (paths within solid line ellipse) and sideways and rearward imaging paths 52 (paths within dashed line ellipse) are illustrated. Front lens group 62 images space 20 and transmits the forward field of view through the rear lens group 64 onto the center portion 66a of image sensor 66. The illuminated space 44 alongside the probe is imaged first by aspherical ring reflector 68 and then by the rear lens group 64, so that the sideways and back fields of view of space 44 are imaged onto the outer or peripheral portion 66b of image sensor 66. The catadioptric objective in the rear lens group 64 is designed so that the central field of the sensor 66 is for forward imaging and the outer ring field of the sensor 66 is for 360 degree omnidirectional sideways and rear imaging. Depending on the angle of aspherical ring reflector 68 relative to the colon wall, the regions imaged can reside only to the side of probe 10 or mostly to the rear of probe 10. The user thus can adjust such angle as well as the angle of ring reflector 42 relative to the colon wall, to obtain only a sideways field of view or a mostly rear or back field of view of the colon wall that are imaged onto portion 66b of sensor 66.

The optical dome 22 can be made from polymethyl methacrylate (PMMA) which has low birefringence and very low autofluorescence when excited at 440 nm. The dome not only protects the optical elements and detector inside the dome, but also serves as the lens holder for the front lens group 62 and the hollow cylindrical light guide 16 for forward illumination. The rear lens group 64 may be contained and mounted onto the hollow cylindrical light guide 16 which serves as a lens holder for group 64. Because both the light guide and optical dome are optically transparent, they do not block the illumination or imaging fields. Thus, as can be readily observed from FIGS. 1 and 2, none of the components of probe 10 blocks the illumination or imaging fields. In other words, the forward illumination path, the sideways and rearward illumination paths and the forward, sideways and rear imaging paths 50 and 52 are unobstructed by any component of the probe 10.

As the relative positions of the forward, sideways and rear imaging fields of view 66a and 66b are fixed spatially on sensor 66, the two video images can be aligned and displayed together so that the endoscopist can easily correlate and determine the location of lesions seen on the rear-view image relative to the forward view image.

Dual-view objectives have been studied by a few research groups. However, the reported dual-view objectives do not have built-in illumination systems. Instead, they rely solely on the external illumination of the standard colonoscope. Please see Waye J D, Heigh R I, Fleischer D E, et al. A retrograde-viewing device improves detection of adenomas in the colon: a prospective efficacy evaluation (with videos). Gastrointestinal Endoscopy. March 2010; 71(3):551-556; Wang R C C, Deen M J, Armstrong D, Fang Q Y. Development of a catadioptric endoscope objective with forward and side views. Journal of Biomedical Optics. June 2011; 16(6); Ma J, Simkulet M, Smith J. C-view omnidirectional endoscope for minimally invasive surgery/diagnostics. SPIE Proceedings. 2007; 6509:65090C; Ryusuke S, Takarou E, Tomio Y. Omnidirectional vision attachment for medical endoscopes. OMNIVIS08. 2008:1-14. Consequently, in these prior art systems, both front illumination and rear-illumination are partially blocked by the objective. In addition, the rear-view is partially blocked by the mechanical lens holder for the front lens group of forward imaging, as explained above. The single image in some of the embodiments of our system is not possible in the competing technologies such as the Third Eye Retroscope which uses two different monitors, requiring the physician to watch two screens at the same time, and making it difficult for the physician to register and localize images.

Polarized illumination and detection can be used in the embodiments of this invention described herein to remove the specular reflection from the mucosa, water and mucin, and to enhance the visibility of diseased tissue. This may be accomplished by placing a polarizer (not shown) between the radiation source (not shown either), and the fiber rings 12 and 14, or by placing an analyzer (i.e. a polarizer) 72 between the imaging optics and the imaging sensor 66. This design also allows lesions to be seen more easily with high contrast by capturing scattered electromagnetic radiation from inside the tissue and removing unwanted specular reflection.

In addition to or in lieu of polarized white light imaging, the system can also incorporate autofluorescence imaging with a range of excitation wavelengths, such as 280 nm, 340 nm, or 440 nm, to improve lesion contrast. For this purpose, an emission filter 74 may be used as in FIG. 2 to block the reflection of the radiation illuminating the forward and back fields of view but transmit radiation emitted by autofluorescence from the forward and back fields of view to sensor 66. Sensor 66 may comprise CMOS devices or CCDs. The positions of the analyzer 72 and emission filter 74 in FIG. 2 may be swapped, and emission filter 74 may be placed anywhere in the imaging paths.

An illumination or excitation filter 99 (such as ones shown in dotted lines in FIG. 1) may also be placed anywhere in the illumination paths of forward path 18 and rearward paths 46 to pass a narrow band of wavelengths for forward and back field of view imaging. The imaging mode of probe 10 is switched by changing the illumination spectrum, such as by choosing the appropriate illumination or excitation filter or emission filter 74.

In this manner, probe 10 is capable of multimodal operation where the appropriate mode of operation can be chosen for any particular application, such as white light, polarized light, fluorescence and narrow-band imaging.

For a numerical aperture on the sensor side of 0.2, the corresponding F/# can be 2.5. In this example, the forward field of view may be +/−45° degrees and the 360° omnidirectional sideways and rear field of view is preferably from 100° to 140° backwards. The two imaging fields share the rear lens group 64 close to the sensor, but not the front group 62 of lenses, which is used only for imaging the forward field of view. The sideways and back field of view is imaged by also reflector 68 and then by the rear lens group 64 onto sensor 66. The imaging fields of view can be tailored for specific applications by different optical prescriptions of the rear lens group 64 and the front lens group 62.

Current Techniques of Increasing Lesion Contrast

Recent advances in endoscopic imaging, such as narrow band imaging (NBI) and flexible imaging color enhancement (FICE) have not improved the polyp detection rate beyond that achieved with high resolution white light endoscopy. High risk serrated lesions are difficult to see as they tend to be sessile or flat and have poor color contrast. Chromoendoscopy can increase the detection of such neoplasms, but it is time consuming, difficult to learn and has not been accepted into clinical practice by busy endoscopists with limited time for procedures. Endoscopes equipped with autofluorescence imaging have been developed to aid the detection of polyps and neoplasms with poor contrast. Small studies have indicated that autofluorescence endoscopes can improve polyp detection, however the results can be further improved with dual-view capability.

Image Overlay

As shown in FIG. 2 and noted above, the central portion 66a of the CMOS sensor 66 captures the image through the front lens group 62 and the outer portion 66b obtains the image from the sideways and/or rear field of view through the reflector 68, which preferably is aspherical. The output signals 80, 82 from the central and outer portions representing the forward and back fields of view may then be processed by a processor 84 which sends signals to a display 86 for displaying the forward, sideways and back fields of view together in the same image 88. We display forward (F) and sideways and/or back (B) fields of view simultaneously on a monitor (FIG. 2) with the central region for forward field of view and the outer ring for 360 degree omnidirectional sideways and/or back field of view. The FR image 88 is displayed on the same monitor 84, alternating with the color image. To the extent that the illuminated and imaged space 44 is large, it covers much of the side field of view also in addition to the rear field of view. One or more of the objectives in the front and rear groups 62, 64 may be a zoom lens, so that the magnification and angles of forward and backward fields of view of the probe for illumination and imaging may be adjusted as desired. The magnification and angles of forward, sideways and backward fields of view of the probe for illumination and imaging may be adjusted also by moving one or more of the lenses in the front and/or rear groups of lenses 62 and 64 in FIGS. 1 and 2 and lenses 152 in FIGS. 5A, 5B.

While probe 10 can be used as a single stand-alone imaging probe or endoscope, it is also compatible for use with any endoscopic and surgical instrument that has a surgical channel as illustrated in FIG. 3A. FIG. 3A is a cross-sectional view of an endoscope with channels for housing an imaging probe to illustrate another embodiment of the invention. FIG. 3B is a perspective view of the distal end of the endoscope of FIG. 3A. As illustrated in FIG. 3A, probe 10 can be passed into an internal instrument channel 102 of an endoscope or laparoscope 100 for use during endoscopy or surgery (laparoscopic or robotic surgery). Alternatively, it can be carried in an external instrument channel 104 of the endoscope or laparoscope 100.

Figure 4A:
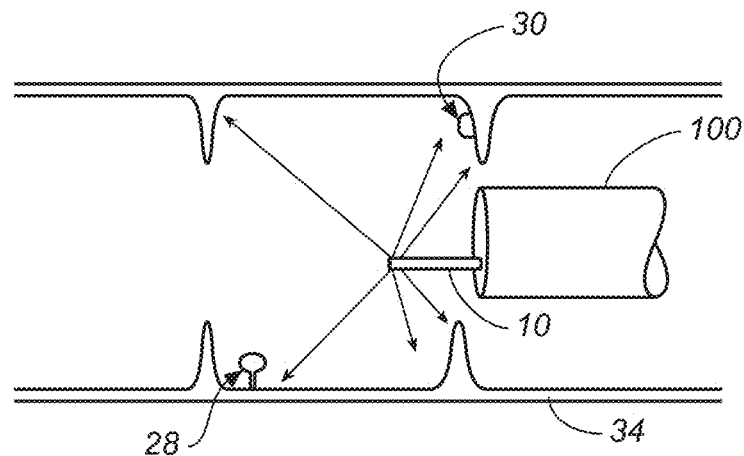
FIG. 4A is a cross-sectional view of the distal end of the endoscope of FIG. 3A in a colon or small intestine for inspecting the colon or small intestine to illustrate how the endoscope is used for inspection.
Figure 4B:
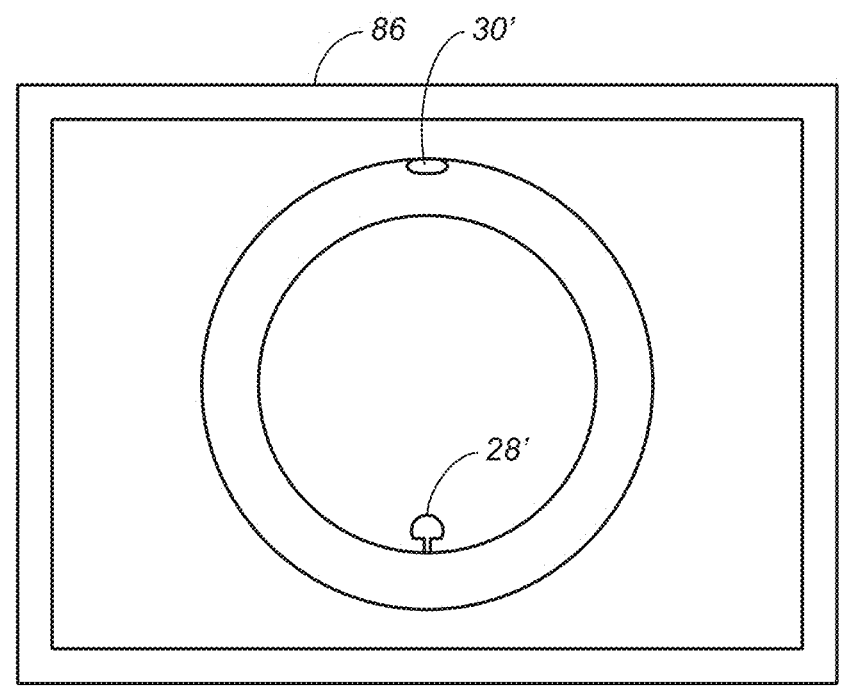
FIG. 4B illustrates a display of the forward, sideways and back fields of view obtained using the endoscope of FIG. 3A for inspecting the colon or small intestine in FIG. 4A.

FIG. 4A is a cross-sectional view of the distal end of the endoscope 100 of FIG. 3A in a colon 34 or small intestine for inspecting the colon or small intestine to illustrate how the endoscope is used for inspection. FIG. 4B illustrates a display of the forward, sideways and back fields of view obtained using the endoscope of FIG. 3A for inspecting the colon or small intestine in FIG. 4A. Thus, in a manner similar to that described above when probe 10 is used as a stand alone inspection probe, probe 10 carried in the endoscope 100 can be used to detect lesions such as lesions 28 in the forward field of view and lesion 30 in the back field of view. A forward field of view (image) 28' of the lesion 28 and a sideways and back field of view (image) 30' of the lesion 30 are displayed as registered images on the same monitor 86. The relative sizes of the respective fields of view can be tailored for a specific application.

Multi-photon Microscopy

For 2- and 3-photon (multi-photon) microscopy, cells or tissue are excited with near simultaneous absorption of two/three long wavelengths. For example, with 2-photon microscopy, the 2 photons have the same effect as a single photon of twice the energy but half the wavelength. The use of longer wavelengths in multi-photon imaging enables deeper penetration of tissue with less damage to the cells at the focal plane. Exogenous fluorescent tags as well as native fluorescence can be targeted to produce high resolution, high contrast images of tissue. This is being rapidly developed for imaging, including fiber-optic in-vivo microscopy. Thus, appropriate wavelengths for the forward and back fields of view illumination may be selected to enable multi-photon microscopy in any one or more of the embodiments of this invention.

Applications

Probe 10 can be inserted and removed repeatedly into the parent or conduit instrument to allow biopsy and surgery to be carried out through the same (single) operating channel of an endoscope. This allows the single channel of the endoscope to be shared for dual-view imaging and biopsy or resection during a single procedure.\

Probe 10 can be easily removed and mucus or debris cleaned if necessary during a procedure without the need to remove the parent/conduit device (laparoscope or endoscope).

Probe 10 can be used during endoscopy or surgery to locate lesions not seen during conventional endoscopy or surgery, with multi-modal capabilities; e.g. the detection of polyps behind folds in the colon and vascular ectasias and tumors hidden behind folds in the small intestine.

Probe 10 can be used in robotic surgery of body cavities such as the thorax to provide dual-view multi-modal imaging, e.g. of the hilum of the lung, or major blood vessels, nerves or vital structures that are not visible with existing instruments that provide limited forward-view imaging.

Probe 10 can be used during endoluminal endoscopic surgery and Natural Orifice Translumenal Endoscopic Surgery (NOTES) to provide currently unavailable forward and backward omnidirectional views.

Probe 10 can be used in multiple sites of the body, e.g., during pelvic surgery, arthroscopy, and examination of the sinuses to provide views of currently unseen areas.

Probe 10 can be used to facilitate the safe and accurate insertion of instruments into body lumens, such the positioning of a double-lumen endotracheal tube during thoracic and lung surgery.

Figure 5A:
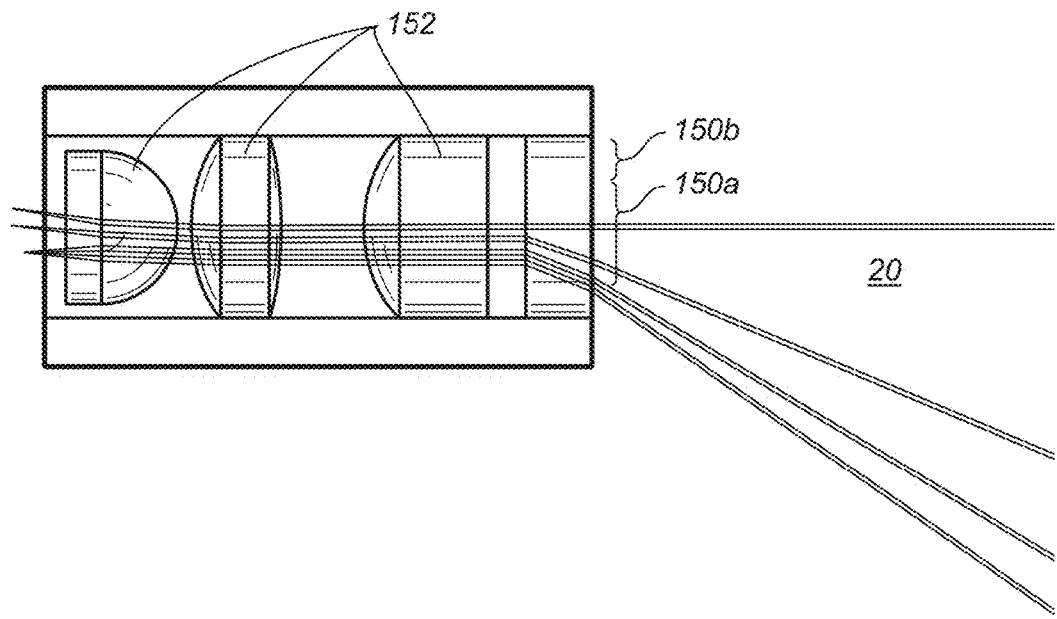
FIG. 5A is a partly cross-sectional and partly perspective view of some of the components of an imaging probe, where the forward imaging paths are illustrated and where the forward, sideways and rearward imaging paths employ the same optical elements to illustrate another embodiment of the invention different from that of FIG. 1.
Figure 5B:
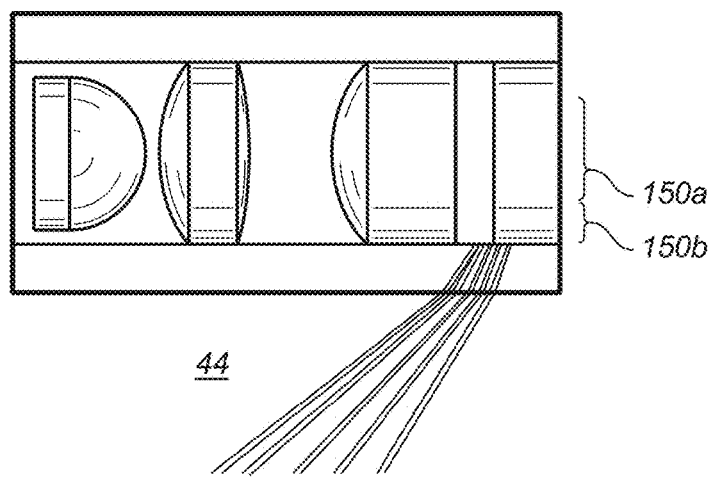
FIG. 5B is a partly cross-sectional and partly perspective view of some of the components of an imaging probe, where the rearward imaging paths are illustrated and where the forward, sideways and rearward imaging paths employ the same optical elements to illustrate the embodiment of FIG. 5A.

Instead of an optical design where the forward and back field of view imaging uses some different elements, in another embodiment, the same optical elements are used in the forward, sideways and back field of view imaging, which is illustrated in FIGS. 5A and 5B. FIG. 5A is a partly cross-sectional and partly perspective view of some of the components of an imaging probe, where the forward imaging paths are illustrated and where the forward, sideways and rearward imaging paths employ the same optical elements to illustrate another embodiment of the invention different from that of FIG. 1. FIG. 5B is a partly cross-sectional and partly perspective view of some of the components of an imaging probe, where the sideways and rearward imaging paths are illustrated and where the forward, sideways and rearward imaging paths employ the same optical elements to illustrate the embodiment of FIG. 5A.

In the embodiment of FIGS. 5A, 5B, optical element 150 comprises a center portion 150a that transmits electromagnetic radiation and a peripheral portion 150b that reflects electromagnetic radiation. Thus, as shown in FIG. 5A, the center portion 150a transmits the electromagnetic radiation from space 20 in front of the probe through lenses 152 towards sensor 66 (not shown). As shown in FIG. 5B, the peripheral portion 150b reflects the electromagnetic radiation from space 44 alongside the probe rearward and through lenses 152 towards sensor 66 (not shown). The embodiment of FIGS. 5A, 5B is advantageous in that the same optical elements are used for forward, sideways and back field of view imaging paths. Aside from the above noted differences, the probe in the embodiment of FIGS. 5A, 5B is similar to that of FIGS. 1 and 2.

Figure 6A:
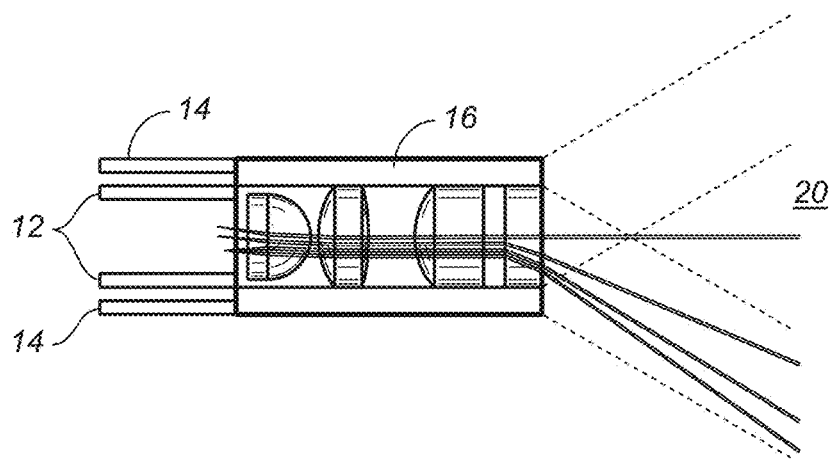
FIG. 6A is a partly cross-sectional and partly perspective view of some of the components of the imaging probe of FIG. 1 for illuminating the inspected areas.
Figure 6B:
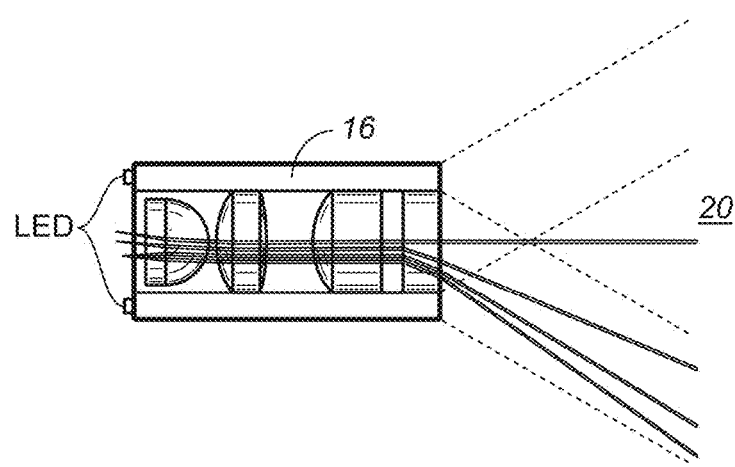
FIG. 6B is a partly cross-sectional and partly perspective view of some of the components of an imaging probe to illustrate another scheme for providing the illumination of the inspected areas.
Figure 6C:
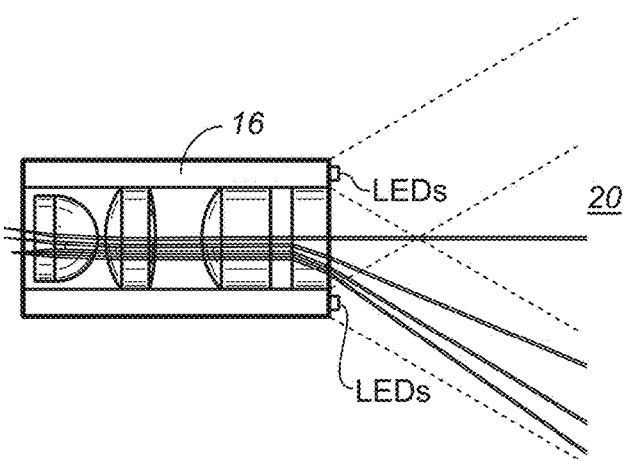
FIG. 6C is a partly cross-sectional and partly perspective view of some of the components of an imaging probe to illustrate yet another scheme for providing the illumination of the inspected areas.

FIG. 6A is a partly cross-sectional and partly perspective view of some of the components of the imaging probe of FIG. 1 for illuminating the inspected areas. In FIG. 6A optical fiber bundles in arrays or rings 12 and 14 are used for supplying electromagnetic radiation. FIG. 6B is a partly cross-sectional and partly perspective view of some of the components of an imaging probe to illustrate another scheme for providing the illumination of the inspected areas. Instead of using optical fiber bundles in arrays or rings 12 and 14 as in FIG. 6A, LEDs may be mounted directly onto or placed close to the hollow light guide 16 or reflector 42 (not shown) to supply electromagnetic radiation. In this embodiment, electromagnetic radiation supplied by the LEDs is transmitted by light guide 16 and emerges as ray 18 as in FIG. 1. FIG. 6C is a partly cross-sectional and partly perspective view of some of the components of an imaging probe to illustrate yet another scheme for providing the illumination of the inspected areas. In this embodiment, electromagnetic radiation supplied by the LEDs bypasses light guide 16 and directly illuminates space 20 in front of the probe.

The embodiments illustrated in FIGS. 5A, 5B, 6B and 6C may be used in any one or more of the applications described herein.

The embodiments of this invention can also be used for remote visual inspection of a large variety of structures or spaces, including: engines of airplanes, automobiles, ships, manufacturing machinery, spacecraft, and power generators, as well as others, through any small opening.

Figure 7:
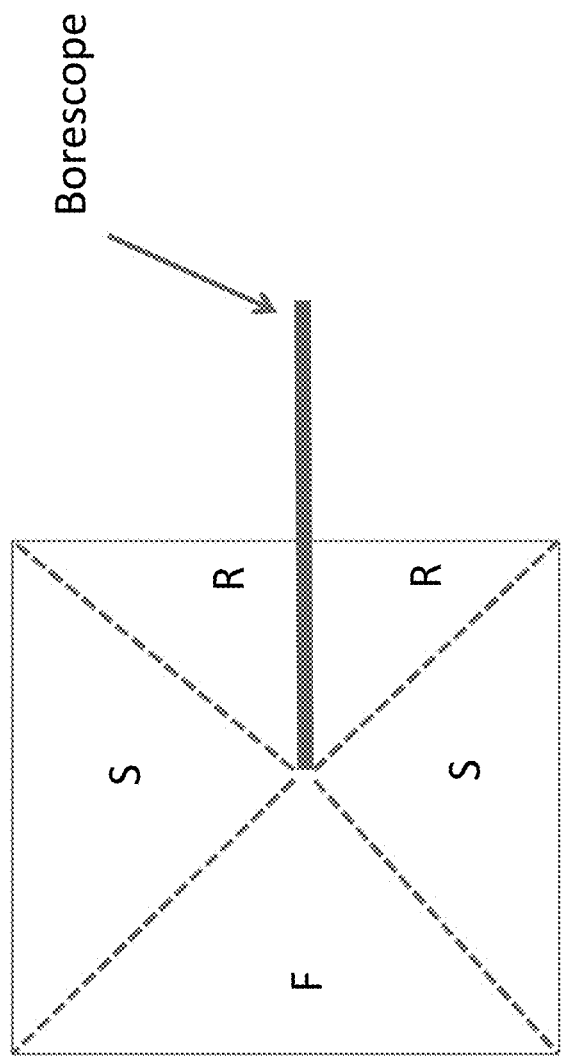
FIG. 7 is a schematic view of a borescope used to inspect a chamber in an instrument such as engine or turbine. The omnidirectional borescope can illuminate and image in forward (F), sideways (S) or rear (R) directions without the need to be flexed or have attachments that provide views in different directions.

FIG. 7 is a schematic view of a borescope used to inspect a chamber in an instrument such as engine or turbine. The omnidirectional borescope can illuminate and image in forward (F), sideways (S) or rear (R) directions without the need to be flexed or have attachments that provide views in different directions.

Figure 8:
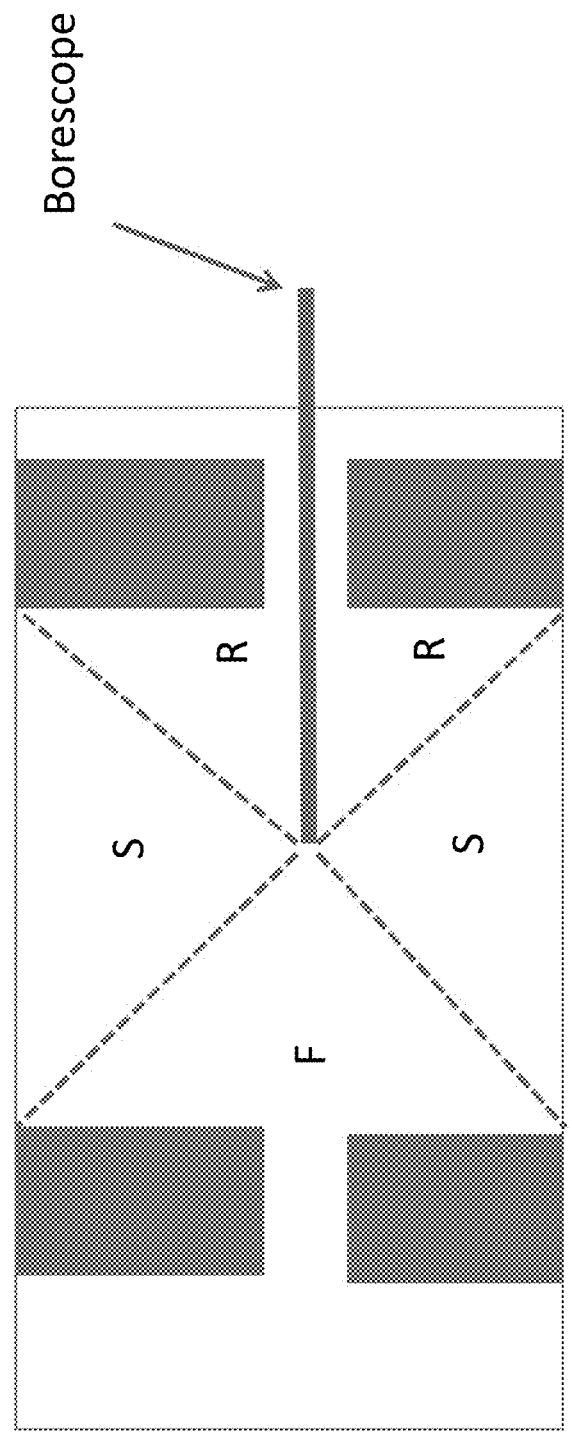
FIG. 8 is a schematic view of a borescope used to inspect a chamber in an instrument such as engine or machine with inner components such as turbine blades (shaded in grey). The omnidirectional borescope can illuminate and image to the front (F), rear (R) as well as to the sides (S) to enable inspection of all surfaces.

FIG. 8 is a schematic view of a borescope used to inspect a chamber in an instrument such as engine or machine with inner components such as turbine blades (shaded in grey). The omnidirectional borescope can illuminate and image to the front (F), rear (R) as well as to the sides (S) to enable inspection of all surfaces.

Figure 9:
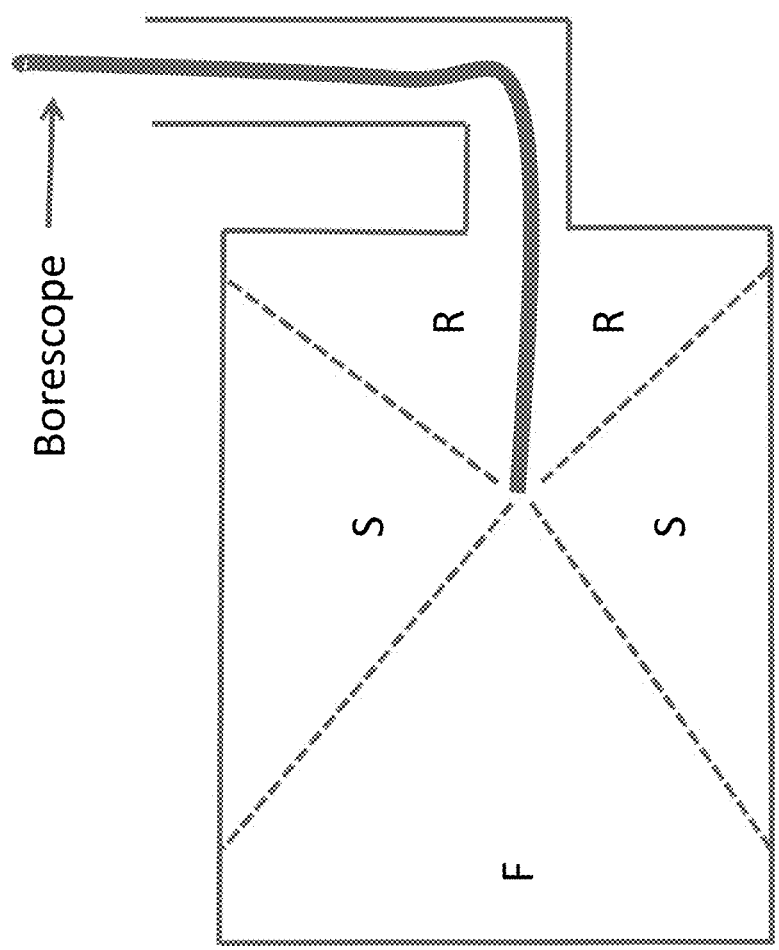
FIG. 9 is a schematic view of a flexible borescope entering a chamber such as an engine or container through a curved entry port, providing illumination and viewing in forward (F), sideways (S) and/or rear (R) directions.

FIG. 9 is a schematic view of a flexible borescope entering a chamber such as an engine or container through a curved entry port, providing illumination and viewing in forward (F), sideways (S) and/or rear (R) directions. The borescopes in FIGS. 7, 8 and 9 may have constructions similar to the probe 10 described above. However, in the case of the borescope FIG. 9, the components of the borescope, such as the cylindrical light guide 16, are made of flexible materials, so that the borescope is capable of being bent along turns in passages. In the same vein the probe 10 in FIG. 1 may be made of flexible materials, so that the probe is capable of being bent along turns in passages, such as those in living body lumens (e.g. the colon and arteries).

The dual-view apparatus can be made of materials that can withstand extreme physical conditions including temperature, pressure, corrosive chemicals and radiation. The dual-view technology can be customized to meet the requirements of specific non-destructive inspection needs.

Non-destructive inspection embodiments of the probe for inspecting living organisms and/or inanimate objects include:

1. A rigid, straight device for dual-view illumination and inspection of an engine or enclosed structure or machinery, or container through narrow opening using electromagnetic radiation. The device may be shaped as a rod.

2. A rigid, straight or curved device for illumination and inspection of an enclosed structure through a narrow opening using electromagnetic radiation. The device may be shaped as a rod.

3. A flexible device for illumination and inspection of an enclosed structure through a narrow opening using electromagnetic radiation.

4. The dual view optical probe can be an independent borescope, or be passed through an introducer or conduit, or built into an existing inspection device.

The dual-view devices can be made of varying diameters to allow insertion through a given port.

Any of the above devices where the illumination can be white light or any band of visible light, or any range or electromagnetic radiation, including ultra-violet and infrared wavelengths. Inspection can include direct visual inspection or the imaging of specific chemical targets, or sensing of temperature from living bodies or inanimate objects (thermal vision). In such event, no radiation will need to be provided to the forward and back fields of vision by guide 16 and fibers 14, and the image sensor 66 may be used to perform forward imaging along a forward path to capture a forward field of view of space in front of the probe onto an image sensor; and to perform rearward imaging along a rearward path to capture a back field of view of space alongside the probe onto the image sensor, so that the forward and back fields of view are registered in a fixed spatial relationship relative to one another on the image sensor. This manner of operation may be useful for visual inspection such as night vision by the imaging of a dark environment such as dark structures or rooms, or the capture of emissions from chemical targets. To perform such operation, some of the components in probe 10 are not needed and may be omitted in its construction, such as fibers 12, 14, guide 16 and front lens group 62.

The embodiments described herein enable combined illumination and imaging of forward and sideways and/or backward views of structures to be made. The image from the image sensor 66 can be displayed directly to the eye, or communicated to a display device, such as a computer, intelligent tablet, cell phone, display panel, intelligent goggles, directly via cables, or wirelessly. The image or information can be transmitted via a secure network or through the internet.

Furthermore, the imaging can be used by illuminating with electromagnetic radiation within and outside the visible spectrum, including one or more of the following: white light, monochromatic visible light, UV light, IR light and NIR light.

Any of the above embodiments where the image can be viewed on a computer or other video display, such as tablet, or phone or portable display screen, or goggles worn by the observer. In any of the above embodiments, the image can be transmitted electronically through cables or transmitted wirelessly. The image can be transmitted to a remote observer through cables, wirelessly, or through a secure network or the internet. The image can also be stored as a digital image or photograph.

While the invention has been described above by reference to various embodiments, it will be understood that changes and modifications may be made without departing from the scope of the invention, which is to be defined only by the appended claims and their equivalents.

What is claimed is:

1. An imaging probe comprising:
a first ring array for supplying electromagnetic radiation in a forward illumination path for illuminating a forward field of view of space in front of the probe, wherein the first ring array is guided by a cylindrical light guide supplying electromagnetic radiation in the forward illumination path to the front end of the probe, and the first ring array, the cylindrical light guide and a front lens group are contained within an optical dome;
a second ring array for supplying electromagnetic radiation in a rearward illumination path for illuminating a 360° omnidirectional primarily back field of view alongside the probe, comprising from 100° to 140° backward relative to a probe axis;
an image sensor; and
an imaging device in imaging paths imaging the forward and the primarily back fields of view onto the image sensor, wherein the forward illumination path, the rearward illumination path and the imaging paths, defined by lenses of a front and of a rear lens group and by a single reflector in each of the rearward illumination path and the imaging paths, are not blocked by any other component of the probe, wherein the forward illumination path, the rearward illumination path and the imaging paths are separated to minimize stray light, wherein a plurality of objectives comprises a first and a second group of objectives, and wherein the first group of objectives comprises the front lens group and the rear lens group, and the second group of objectives comprises the reflector in the rearward imaging path and the rear lens group, and the forward and the primarily back fields of view are discontinuous and imaged respectively by the first and second groups of objectives onto the image sensor; and optionally wherein the forward and the primarily back fields of view are registered in a fixed spatial relationship relative to one another on the image sensor.

2. The probe of claim 1, wherein said imaging device includes an element having a central portion that is transmissive and a peripheral portion that is reflective.

3. The probe of claim 2, wherein said transmissive portion transmits electromagnetic radiation in the forward field of view in front of the probe and the peripheral portion reflects electromagnetic radiation in the primarily back field of view of space alongside the probe.

4. The probe of claim 1, wherein the rear lens group is contained and mounted on the cylindrical light guide.

5. The probe of claim 1, wherein the imaging device images the forward and the primarily back fields of view so that the forward and the primarily back fields of view are registered in a fixed spatial relationship relative to one another on the image sensor.

6. The probe of claim 5, further comprising a processor that constructs and displays the registered forward and the primarily back fields of view on a display.

7. The probe of claim 1, wherein the imaging device includes a zoom lens so that the magnification of the imaging device is adjustable.

8. The probe of claim 1, wherein the first and second ring arrays each include a light guide, the probe further comprising LEDs located adjacent to the light guides of the first and second elements.

9. The probe of claim 1, wherein the first d second ring arrays each include at least one LED.

10. The probe of claim 1, wherein the electromagnetic radiation supplied by the second ring array for illumination of space alongside the probe is omnidirectional.

11. The probe of claim 1, wherein the first or second ring array comprises an illumination or excitation filter.

12. The probe of claim 1, wherein the imaging device comprises an emission filter.

13. The probe of claim 1, wherein the electromagnetic radiation supplied in the forward illumination path or rearward illumination path is polarized.

14. The probe of claim 1, wherein the probe is configured as a borescope.

15. The probe of claim 1, wherein the light guide is flexible so that the probe is capable of being bent along turns in passages.

16. The probe of claim 1, wherein the probe has a shape of a straight or curved rod.

17. The probe of claim 1, wherein the electromagnetic radiation includes wavelengths in one or more of the following: white light, monochromatic visible light, UV light, IR light, and NIR light.

18. The probe of claim 1, wherein the probe comprises materials that can withstand extreme physical conditions including temperature, pressure, corrosive chemicals, and radiation.

19. The probe of claim 1, further comprising a display for displaying an image from the image sensor.

20. The probe of claim 19, wherein the display includes an intelligent tablet, or a phone or a portable display screen, or an intelligent goggle to be worn by an observer.

21. The probe of claim 19, wherein the display communicates with said image sensor through a cable or wireless transmission.

22. The probe of claim 19, wherein the display communicates with the image sensor through Internet or a secure network.

23. The probe of claim 1, further comprising a housing defining a plurality of channels therein, and wherein the imaging probe is in one of said channels or attached to the housing to provide a medical instrument.

24. The probe of claim 23, wherein said medical instrument is an endoscope, a laparoscope, or an arthroscope.

25. An imaging method, comprising:
supplying, using a first ring array, electromagnetic radiation in a forward illumination path for illuminating a forward field of view of space in front of an imaging probe, wherein the first ring array is guided by a cylindrical light guide supplying electromagnetic radiation in the forward illumination path to the front end of the probe, and the first ring array, the cylindrical light guide and a front lens group are contained within an optical dome;

supplying, using a second ring array, electromagnetic radiation in a rearward illumination path for illuminating a 360° omnidirectional primarily back field of view alongside the probe, comprising from 100° to 140° backward relative to a probe axis;

imaging, using an imaging device, along imaging paths the forward and the primarily back fields of view onto an image sensor, wherein the forward illumination path, the rearward illumination path, and the imaging paths, defined by lenses of a front and of a rear lens group and by a single reflector in each of the rearward illumination path and the imaging paths, are not blocked by any other component of the probe, wherein the forward illumination path, the rearward illumination path and the imaging paths are separated to minimize stray light, wherein a plurality of objectives comprises a first and a second group of objectives, and wherein the first group of objectives comprises the front lens group and the rear lens group, and the second group of objectives comprises the reflector in the rearward imaging path and the rear lens group, and the forward and the primarily back fields of view are imaged respectively by the first and second groups of objectives onto the image sensor; and optionally wherein the forward and the primarily back fields of view are discontinuous and registered in a fixed spatial relationship relative to one another on the image sensor.

26. The method of claim 25, wherein the electromagnetic radiation supplied in the forward and rearward paths is white light, polarized electromagnetic radiation, narrow band electromagnetic radiation, fluorescence, or electromagnetic radiation selected for multi-photon imaging.

27. The method of claim 25, further comprising adjusting a magnification of the imaging.

28. The method of claim 27, wherein the adjusting is means of adjusting a zoom lens.

29. The method of claim 25, further comprising adjusting the forward field of view of space in front of the probe, or the primarily back field of view of space alongside the probe, or both.

30. The method of claim 29, wherein the adjusting is by means of moving one or more objectives in the forward field of view, rearward field of view, and imaging paths.

31. The method of claim 25, wherein the electromagnetic radiation is supplied to illuminate a cavity or passage in a living organism, and the imaging provides an image of the cavity or passage.

32. The method of claim 25, wherein the electromagnetic radiation is supplied to illuminate a chamber or passage in an inanimate environment, and the imaging provides an image of the chamber or passage.

33. The method of claim 25, comprising:
  imaging along the forward path the forward field of view of space in front of the probe onto the image sensor; and
  imaging along the rearward path the primarily back field of view of space alongside the probe onto the image sensor so that the forward and the primarily back fields of view are registered in a fixed spatial relationship relative to one another on the image sensor.

34. The method of claim 33, wherein the imaging senses a temperature of living bodies or of inanimate objects.

35. The method of claim 33, wherein the imaging captures radiation in a dark environment.

36. The method of claim 33, wherein the imaging captures radiation from a chemical target.

37. The method of claim 25, wherein the reflector in the rearward illumination path comprises a ring reflector reflecting electromagnetic radiation from the second ring array in the rearward illumination path.

38. The imaging probe of claim 1, wherein the reflector in the rearward illumination path comprises a ring reflector reflecting electromagnetic radiation from the second ring array in the rearward illumination path direction.

* * * * *